United States Patent
Kinnear et al.

(10) Patent No.: US 6,719,744 B2
(45) Date of Patent: Apr. 13, 2004

(54) ELASTIC CLOSURE TAPE TAB FOR DISPOSABLE ABSORBENT ARTICLES SUCH AS DIAPERS

(75) Inventors: Christopher M. Kinnear, Wales (GB); Stuart L. Eynon, South Wales (GB)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 10/204,755
(22) PCT Filed: Mar. 5, 2001
(86) PCT No.: PCT/US01/07015
§ 371 (c)(1), (2), (4) Date: Aug. 22, 2002
(87) PCT Pub. No.: WO01/68025
PCT Pub. Date: Sep. 20, 2001

(65) Prior Publication Data
US 2003/0032359 A1 Feb. 13, 2003

(30) Foreign Application Priority Data
Mar. 15, 2000 (EP) .............................. 00200919

(51) Int. Cl.⁷ ................................. A61F 13/15
(52) U.S. Cl. ................ 604/389; 604/390; 604/387; 604/386; 604/391
(58) Field of Search ..................... 604/389, 390, 604/391, 386, 387

(56) References Cited

U.S. PATENT DOCUMENTS

| | | |
|---|---|---|
| 3,265,765 A | 8/1966 | Holden et al. |
| 3,276,944 A | 10/1966 | Levy |
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,562,356 A | 2/1971 | Nyberg et al. |
| 3,692,618 A | 9/1972 | Dorschner et al. |
| 3,700,633 A | 10/1972 | Wald et al. |
| 3,800,796 A | 4/1974 | Jacob |
| 4,036,233 A | 7/1977 | Kozak |
| 4,116,917 A | 9/1978 | Eckert |
| 4,156,673 A | 5/1979 | Eckert |
| 4,340,653 A | 7/1982 | Adams |
| 4,857,067 A | 8/1989 | Wood et al. |
| 5,019,073 A | 5/1991 | Roessler et al. |
| 5,176,671 A | 1/1993 | Roessler et al. |
| 5,182,156 A * | 1/1993 | Pape et al. |
| 6,051,094 A * | 4/2000 | Melbye et al. |

FOREIGN PATENT DOCUMENTS

| | | |
|---|---|---|
| EP | 0 247 855 B1 | 3/1992 |
| EP | 0 529 681 A1 | 3/1993 |
| EP | 0 324 578 B1 | 7/1993 |
| EP | 0 563 457 A1 | 10/1993 |
| EP | 0 563 458 A1 | 10/1993 |
| EP | 0 704 196 A1 | 4/1996 |
| EP | 0 487 758 B1 | 3/1997 |
| WO | 96/10382 | 4/1996 |
| WO | 99/48455 | 9/1999 |

* cited by examiner

Primary Examiner—Weilun Lo
Assistant Examiner—Jacqueline F Stephens
(74) Attorney, Agent, or Firm—Gary L. Griswold; Robert W. Sprague; William J. Bond

(57) ABSTRACT

The present invention provides an adhesive closure tape tab (10,50) form of an elastic laminate (15) of an elastic film (16) having on at least a first major side an expandable fibrous layer (17) of non-woven thermoplastic polymer fibers. On the second major side of the plastic film are attached, a first (30) and a second (20) non-elastic adhesive tape. Each adhesive tape is formed of a fibrous layer (21) of non-woven thermoplastic polymer fibers having on one major surface an adhesive layer (22). The first (30) and second (20) non-elastic adhesive tape are attached opposite to each other to the second major side of the elastic laminate (15) by an adhesive layer (22) and extending beyond the elastic laminate (15).

7 Claims, 6 Drawing Sheets

ELASTIC CLOSURE TAPE TAB FOR DISPOSABLE ABSORBENT ARTICLES SUCH AS DIAPERS

FIELD OF THE INVENTION

The present invention relates to an adhesive closure tape tab for manufacturing absorbent articles such as diapers. In particular, the invention relates to an adhesive closure tape tab that comprises an elastic laminate. The invention further relates to a prelaminated composite tape in stable roll form from which an adhesive closure tape tab can be cut. The invention further provides an absorbent article comprising the adhesive closure tape tab according to the invention.

BACKGROUND OF THE INVENTION

A disposable diaper typically has a thin, flexible, stretchy, low density polyethylene backsheet film, an absorbent core on the inside of the backsheet film, and a porous top sheet overlying the core. Such a diaper is positioned at the crotch of the wearer, the two ends of the diaper extending, respectively toward the front and back. Adjacent edges of the diaper at each side are then either positioned adjacent to each other or overlapped, a strip of pressure-sensitive adhesive tape or mechanical fastener tape being adhered to the back sheet at the border adjacent each of the two edges, holding the diaper closed.

A desirable closure system which is used for disposable articles employs a mechanical fastener, comprising for example, hook and loop fastening components. Mechanical fastening systems have the advantage that they may be repeatedly used for opening and refastening the disposable article. Closure systems which contain mechanical fasteners are described in U.S. Pat. Nos. 5,019,073 and 5,176,671, in European patent applications EP 324 578, EP 563 457 and EP 563 458 and in WO 96/21413.

The exterior of disposable absorbent articles, in particular diapers, nowadays is often a non-woven to give the diaper a cloth like feel. Accordingly, desirable closure systems for use with these diapers preferably also have a non-woven backing so as to have a cloth like feel for the diaper closure system as well. Furthermore, developments have taken place to include elasticity in the closure system which increases the comfort of the wearer of the disposable absorbent article.

WO 99/48455 for example discloses an elastic tab laminate that can be adhered to the edge of an absorbent article. The elastic tab laminate is formed using a co-extruded elastic film comprising at least one elastic layer that has on one face a partially extensible non-woven layer. At the other face, there is provided a pressure sensitive adhesive layer and/or a component of a mechanical fastener system.

EP 704 196 discloses a fastening tape for a disposable diaper. The fastening tape includes a stretchable elastic material secured to one surface of the tape at least at both ends thereof thereby bridging a section of the fastening tape. The length of the fastening tape bridged by the elastic tape is longer that the elastic tape in its relaxed state.

However, the elastic tab laminate and fastening tape disclosed in these two patent applications have the disadvantage that tie skin of the wearer may be exposed to the elastic film which may cause irritation of the skin because the film may rub over the skin during repeated expansion and relaxation of the elastic film. This will in particular be the case with sensitive skins such as the skin of babies. Accordingly, it would be desirable to develop an elastic closure tape tab that would not have this disadvantage and that at the same time provides a good performance, i.e. provides good elasticity and reliable closing of the disposable absorbent article and that is compatible with existing manufacturing methods of disposable absorbent articles. Preferably, the elastic closure tape tab can be manufactured in an easy and cost effective way.

DISCLOSURE OF THE INVENTION

The present invention provides in one aspect, an adhesive closure tape tab that comprises an elastic laminate of an elastic film that has on at least a first major side an expandable fibrous layer of non-woven thermoplastic polymer fibers. The adhesive closure tape tab can be easily manufactured and is compatible with existing manufacturing equipment. Moreover, the adhesive closure tape tabs of the present invention are less irritating for the skin and therefore provide more comfort to the wearer of an adsorbent article having an adhesive closure tape tab according to this invention.

In a preferred embodiment, the expandable fibrous layer of the elastic laminate of the adhesive closure tape tab according to this invention is provided on both major sides of the elastic film. By the term expandable fibrous layer is meant that the fibrous layer can be expanded when the elastic film to which the fibrous layer is secured is stretched. Since the fibrous layer itself is non-elastic, the expandability of the layer is achieved by securing a fibrous layer to the elastic film such that the length of the fibrous layer is longer than the length of the elastic film in its relaxed state. Accordingly, it will be possible to expand the fibrous layer upon stretching of the elastic film until the elastic film is stretched to a length equal to the length of the fibrous layer. Stretching beyond this limit will require substantial increase in the stretch force because it would require deformation of the fibrous layer. The fibrous layer is generally coextensive with the elastic film and will preferably have an expandability of at least 30% and preferably at least 75%, that is to say that the elastic laminate can be stretched by at least 30% and preferably at least 75% of its length in the relaxed state. Typically, the expandability of the fibrous layer is between 50 and 400% and most preferably between 75% and 200%.

The fibrous layer is secured to the elastic film in intervals, i.e. when viewed in the longitudinal direction, portions of the fibrous layer that are connected to the elastic film are alternated with portions of the fibrous layer that are not connected to the elastic film layer. This may be achieved by a technique called ringrolling as disclosed in EP 704196 or alternatively, by corrugating the fibrous layer to form arcuate portions and anchor portions therein and then extruding a molten thermoplastic material thereon that forms the elastic film when cooled. This latter technique is described in detail in WO 99/48455.

The elastic film comprises a material that exhibits elastomeric properties at ambient conditions, i.e. the material will substantially resume its original shape after being stretched. Preferably, the elastomer will sustain only a small permanent set following deformation and relaxation, which set is preferably less than 30% and more preferably less than 20% of the original 50% to 500% stretch. The elastomeric material can be either pure elastomers or blends with an elastomeric phase or content that will still exhibit substantial elastomeric properties at room temperature. Suitable elastomeric thermoplastic polymers include block copolymers or the like. These block copolymers are described in for example U.S. Pat. Nos. 3,265,765; 3,562,356; 3,700,633;

4,116,917 and 4,156,673. Particularly useful are styrene/ isoprene, butadiene or ethylene-butylene/styrene block copolymers. Generally, the block copolymers contain an A block and a B block. These blocks may be arranged in any order including linear, radial, branched or star block copolymers. Other useful elastomeric compositions can include elastomeric polyurethanes, ethylene copolymers such as ethylene vinyl acetates, ethylene/propylene copolymer elastomers or ethylene/propylene/diene terpolymer elastomers. Blends of these elastomers with each other or with modifying elastomers are also contemplated.

Viscosity reducing polymers and plasticizers can also be blended with the elastomers such as low molecular weight polyethylene and polypropylene polymers and copolymers, or tackifying resins such as Wingtack™, aliphatic hydrocarbon tackifiers available from Goodyear Chemical Company. Examples of tackifiers include aliphatic or aromatic hydrocarbon liquid tackifiers, polyterpene resin tackifiers, and hydrogenated tackifying resins. Aliphatic hydrocarbon resins are preferred.

Additives such as dyes, pigments, antioxidants, antistatic agents, bonding aids, antiblocking agents, slip agents, heat stabilizers, photostabilizers, foaming agents, glass bubbles, reinforcing fiber, starch and metal salts for degradability or microfibers can also be blended into the elastomeric composition for making the elastic film.

In a preferred embodiment in connection with the present invention, the elastic film comprises an elastomeric core layer of elastomeric material provided on one or both major surfaces with a skin layer. Such a multilayer film can conveniently be produced through co-extrusion. The use of a skin layer is particularly useful on the side where the non-elastic adhesive tape is being attached because the skin layer may function as a barrier layer to migration of tackifiers and other low molecular weight species into the elastic core layer and also creates a more stable surface for the attachment of the non-elastic adhesive tapes, particularly when the skin layer is an inelastic material.

The skin layers can be stretched beyond an elastic limit of these skin layers. The skin layers are generally nontacky materials or blends formed of any semicrystalline or amorphous polymer(s) which are less elastomeric than the elastic core layer, generally inelastic, and which will undergo relatively more permanent deformation than the elastic core layer at the percentage that the elastic film is stretched. Elastomeric materials such as olefinic elastomers, e.g. ethylene-propylene elastomers, ethylene propylene diene polymer elastomers, metallocene polyolefin elastomers or ethylene vinyl acetate elastomers, or styrene/isoprene, butadiene or ethylene-butylene/styrene (SIS, SBS, SEBS) block copolymers, or polyurethanes or blends with these materials can be used as long as the skin layers provided are generally nontacky and preferably can act as barrier layers to any adhesive applied. Generally, the elastomeric materials used are present in a blend with nonelastomeric materials in a weight percent range of 0–70%, preferably 5–50%. High percentages of elastomer in the skin layer(s) generally require of antiblock and/or slip agents to reduce the surface tack and roll unwind force. Preferably, these skin layers are polyolefinic formed predominately of polymers such as polyethylene, polypropylene, polybutylene, polyethylene-polypropylene copolymer, however, these skin layers may also be wholly or partly polyamide, such as nylon, polyester, such as polyethylene terephthalate, or the like, and suitable blends thereof. Generally, the skin layer material following the stretching and recovery of the coextruded elastic is in contact with the elastic core layer material in at least one of three suitable modes; first, continuous contact between the elastic core layer and the microtextured skin layer; second, continuous contact between the layers with cohesive failure of the core layer material under the microtextured skin folds; and third, adhesive failure of the skin layer to the core layer under the microtextured folds with intermittent skin layer to core layer contact at the microtexture fold valleys. Generally, in the context of the present invention, all three forms of skin-to-core contact are acceptable. However, preferably the skin and core layers are in substantially continuous contact so as to minimize possibility of delamination of the skin layer(s) from the elastic core layer.

Generally, the overall elastic core layer to skin layer(s) thickness ratio of the elastic film will be at least 1.5, preferably at least 5.0 but less than 1000 and most preferably from 5.0 to 200. Generally, the overall caliper of the multilayer elastic film is preferably 25 to 200 microns. The addition of the skin layer materials generally tends to reinforce the elastic film material. However, in the present invention the skin layers are provided to be sufficiently thin and/or soft so that little or no reinforcement of the elastomeric core layer occurs and the film is elastic in its initial elongation as well as its second and subsequent elongations at suitably low stress elongation forces and low hysteresis loss levels when the elastic is cycled in use (e.g. by dimensional changes caused by breathing).

Generally, the elastic film has elastic properties on its first and preferably its subsequent elongations similar to that of the elastomeric layer material itself with no distinct yield point or range in the first elongation.

The fibrous layer of the elastic laminate is typically a nonwoven web of thermoplastic polymer fibers. Suitable processes for making, the nonwoven web include, but are not limited to, airlaying, spunbond, spunlace, bonded melt blown webs and bonded carded web formation processes. Spunbond nonwoven webs are made by extruding a molten thermoplastic as filaments from a series of fine die orifices in a spinneret. The diameter of the extruded filaments is rapidly reduced under tension by, for example, non-eductive or eductive fluid-drawing or other known spunbond mechanisms, such as described in U.S. Pat. No. 4,340,653 (Appel et al.); U.S. Pat. No. 3,692,618 (Dorschner et al.); U.S. Pat. No. 3,338,992 and U.S. Pat. No. 3,341,394 (Kinney); U.S. Pat. No. 3,276,944 (Levy); U.S. Pat. No. 3,502,538 (Peterson); U.S. Pat. No. 3,502,763 (Hartman); and U.S. Pat. No. 3,542,615 (Dobo et al.). The spunbond web is preferably bonded. The nonwoven web layer also may be made from bonded carded webs. Carded webs are made from separated staple fibers, which fibers are sent through a combing or carding unit which separates and aligns the staple fibers in the machine direction so as to form a generally machine direction-oriented fibrous nonwoven web. However, randomizers can be used to reduce this machine direction orientation. Once the carded web has been formed, it is then bonded by one or more of several bonding methods to give it suitable tensile properties. One bonding method is powder bonding wherein a powdered adhesive is distributed through the web and then activated, usually by heating the web and adhesive with hot air. Another bonding method is pattern bonding wherein heated calender rolls or ultrasonic bonding equipment are used to bond the fibers together, usually in a localized bond pattern though the web can be bonded across its entire surface if so desired. Generally, the more the fibers of a web are bonded together, the greater the nonwoven web tensile properties.

Airlaying is another process by which fibrous nonwoven webs useful in the present invention can be made. In the airlaying process, bundles of small fibers usually having lengths ranging between about 6 to about 19 millimeters are separated and entrained in an air supply and then deposited onto a forming screen, often with the assistance of a vacuum supply. The randomly deposited fibers are then bonded to one another using, for example, hot air or a spray adhesive.

Alternatively known melt blown webs or spunlace nonwoven webs or the like can be used to form the fibrous layer of the elastic laminate. Melt blown webs are formed by extrusion of thermoplastic polymers from multiple die orifices, which polymer melt streams are immediately attenuated by hot high velocity air or steam along two faces of the die immediately at the location where the polymer exits from the die orifices. The resulting fibers are entangled into a coherent web in the resulting turbulent airstream prior to collection on a collecting surface. Generally, to provide sufficient integrity and strength for the present invention, melt blown webs must be further bonded such as through air bonding, heat or ultrasonic bonding as described above.

In accordance with the present invention, a first and a second non-elastic adhesive tape are attached opposite of each other to the elastic film such that on the first major side the elastic film comprises the expandable fibrous layer and on the second major side, the first and second non-elastic adhesive tape are attached. The first and second non-elastic adhesive tape each comprise a fibrous layer and an adhesive layer. The fibrous layer of the non-elastic adhesive tapes may be prepared as describe above and is generally a dimensionally stable layer having a thickness that is typically between 10 and 150 $g/m^2$ and preferably between 20 $g/m^2$ and 150 $g/m^2$. The fibrous layer of the non-elastic adhesive tapes preferably does not allow the adhesive of the adhesive layer on one side to blead through to the other side. Alternatively, if the fibrous layer would allow adhesive to blead through, a film barrier layer could be provided between the adhesive layer and the fibrous layer. Such a film barrier layer could also be provided to improve the strength of the adhesive tape if the fibrous layer in itself does not provide sufficient strength. The adhesive layer is used to secure the non-elastic adhesive tape to the elastic film. The adhesive layer can be any conventional solution or hot-melt coated adhesive such as a tackified synthetic rubber resin adhesive, an acrylate adhesive, a silicone adhesive, a polyalpha-olefin adhesive, blends and the like. The first and second non-elastic adhesive tape are each secured at one end of the elastic laminate such that a portion of each adhesive tape extends beyond the elastic film. Accordingly, the extended portion of the first or second non-elastic adhesive tape may be used to attach the adhesive closure tape tab to one edge of a disposable absorbent article such as a diaper whereas the extending portion of the other non-elastic adhesive tape will comprise the closure system.

In accordance with one embodiment in connection with the present invention, the closure system may simply consist of the extending portion of one of the non-elastic adhesive tapes. Accordingly, the adhesive layer of the non-elastic adhesive tapes will, in such a system, be used to close the absorbent article by attachment of the extending portion of that non-elastic adhesive tape to a landing zone adapted therefor on the front of the absorbent article. Alternatively, the closure system will comprise a mechanical fastener. In the latter case the extended portion of one of the first and second non elastic adhesive tape will be provided with one of the two mutually engaging means of the mechanical fastener system, typically the hook part of a hook and loop mechanical fastener system. The loop component will generally be formed by the outer surface of the absorbent article.

According to a preferred embodiment, the fibrous layer of the non-elastic adhesive tape is provided on the side opposite to the side having the adhesive layer, with a release layer. It is particularly desirable when the adhesive closure tape tabs are to be stacked on top of each other such as for example in a roll of prelaminated composite tape from which the adhesive closure tape tabs of the invention can be cut. In such a prelaminated composite tape in roll form, the first and second non-elastic adhesive tapes and the elastic film extend axially so that by cutting a piece from the roll, an adhesive closure tape tab with the desired width can be obtained (the length of the adhesive closure tape tab being determined by the width of the roll). Suitable release coatings that can be provided on the fibrous layer of the non-elastic adhesive tapes are well-known to those skilled in the art and include for example UV-curable silicone release coatings and polyurethane based silicone release coatings.

The first and second non-elastic adhesive tapes may be the same or different and may comprise further layers. For example, there may be provided a film layer between the adhesive layer and the fibrous layer of the non-elastic adhesive tapes.

BRIEF DESCRIPTION OF THE DRAWINGS

The present invention is further described with reference to the following drawings that illustrate preferred embodiments according to the present invention without the intention to limit the invention thereto.

DETAILED DESCRIPTION OF PREFERRED EMBODIMENTS

Figure 1:
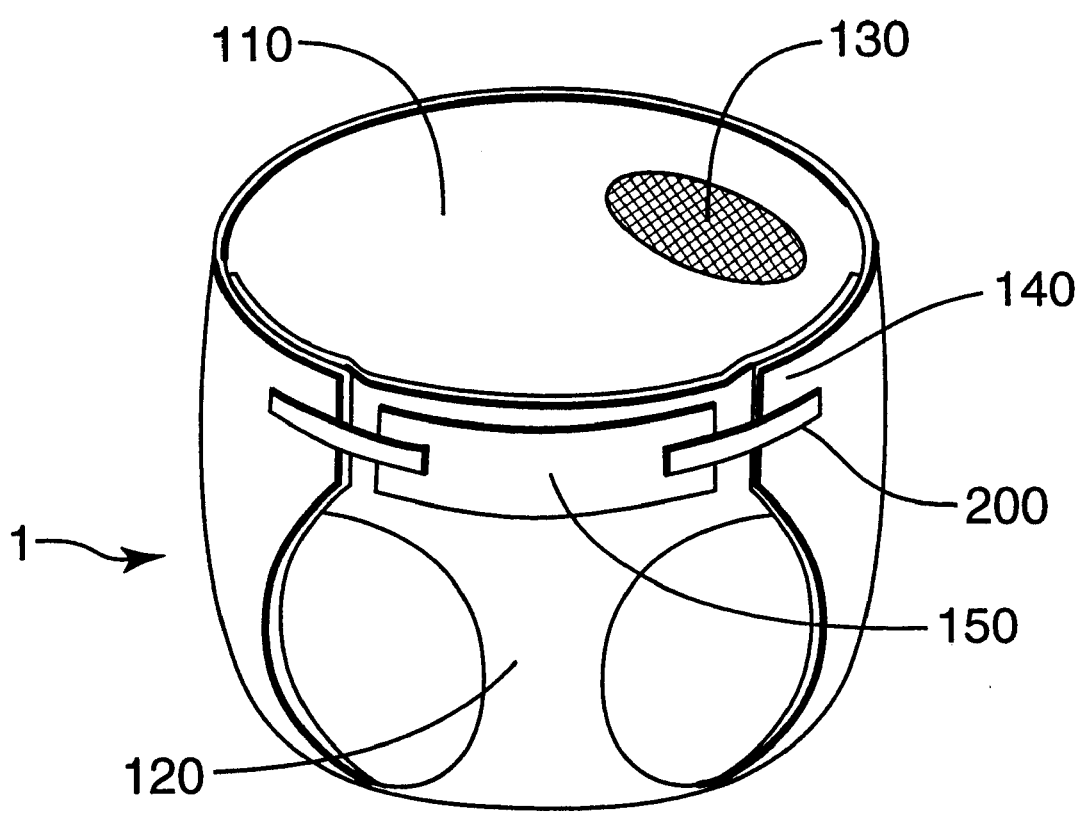
FIG. 1 is a schematic drawing of a disposable absorbent article having adhesive closure tape tabs in accordance with the invention.

The adhesive tape of the present invention is intended for the manufacture of a closure system on an absorbent article and in particular a closure system on a diaper. FIG. 1 is a perspective view of a disposable diaper 1 in a closed form. The diaper comprises an absorbent core 130 between an inside surface 110 and an outside surface 120. The absorbent core 130 may be any means which is generally compressible, conformable, non-irritating to the wearer's skin, and capable of absorbing and retaining liquids and certain body exudates.

The outside surface 120 of the diaper is impervious to liquids and is preferably manufactured from a thin plastic film, although other flexible, liquid-impervious materials may also be used. The outside surface 120 prevents the exudates, absorbed and contained in the absorbent core, from soiling articles which contact the diaper 1, such as bed sheets and undergarments. Outside surface 120 preferably has a cloth like feel.

The inside surface 110 of the diaper is complaint, soft-feeling, and non-irritating to the wearer's skin. Further, the inside surface 110 is liquid-pervious, permitting liquids to readily penetrate through its thickness. A suitable inside surface 110 may be manufactured from a wide range of materials such as porous foams, reticulated foams, apertured films, natural fibers (e.g. wood or cotton fibers), synthetic fibers (e.g. polyester or polypropylene fibers) or from a combination of natural and synthetic fibers. Preferably, it is made of a hydrophobic material to isolate the wearer's skin from liquids retained in the absorbent core 130. A suitable inside surface 110 may be, for example, a spun-bond or carded polypropylene non-woven of approximately 15–25 g/m².

The absorbent core 130 may be secured to the outside surface 120 by means of, for example, pressure-sensitive adhesives, hot melt adhesives or other adhesives, ultrasonic bonding or heat/pressure sealing. The outside surface 120 and the inside surface 110 may be joined to each other directly or indirectly by using an intermediate fixing member to which the outside surface 120 and the inside surface are affixed. The inside surface 110 and the outside surface 120 may be associated together by various means comprising, for example, pressure-sensitive adhesives, hot melt adhesives or other adhesives, ultrasonic bonding and/or heat and/or pressure.

The above description of the diaper 1 is meant to be explanatory only and not limiting. Further details on diapers and their construction are described in literature and may be taken, for example, from EP 0 529 681, U.S. Pat. No. 4,036,233, EP 0 487 758, WO 96/10382, U.S. Pat. No. 3,800,796, EP 0 247 855 or U.S. Pat. No. 4,857,067.

Figure 2:
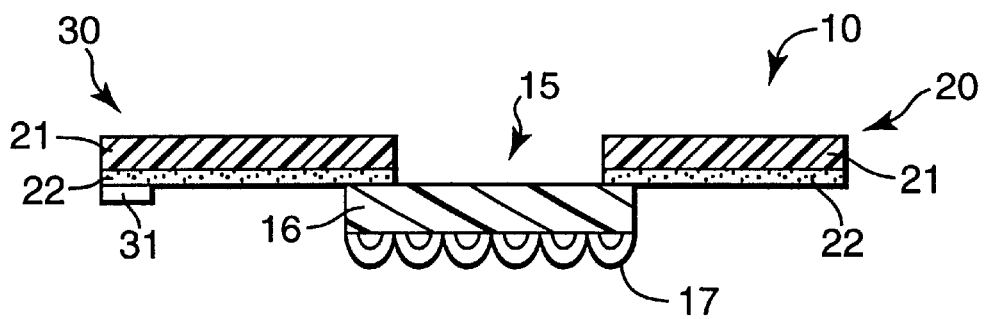
FIGS. 2 and 3 are schematic cross-sectional views of two embodiments of an adhesive closure tape tab according to the invention.

FIG. 2 shows a first embodiment of an adhesive closure tape tab 10 in accordance with the present invention. Adhesive closure tape tab 10 comprises an elastic laminate 15 and first and second non-elastic adhesive tapes 20 and 30 respectively. The elastic laminate 15 comprises an elastic film 16 that has on one major side a fibrous layer 17. The elastic film 16 may consist of a single layer or preferably, the elastic film 16 is a multilayer material comprising a core elastic layer having on one or both sides a skin layer as described above. The fibrous layer 17 is expandable, i.e. has a length that is longer than the length of elastic film 16 in its relaxed state. The fibrous layer 17 is secured to the elastic film in intervals, i.e. when viewed in the longitudinal direction, portions of the fibrous layer that are connected to the elastic film are alternated with portions (shown as are portions in FIG. 2) of the fibrous layer that are not connected to the elastic film layer.

On the other side of the elastic film 16, the non-elastic adhesive tapes 20 and 30 are bonded. The non-elastic adhesive tapes 20 and 30 are bonded opposite each other, each at one edge of the elastic laminate 15. As can been seen from FIG. 2, the non-elastic adhesive tapes 20 and 30 extend beyond the edges of the elastic laminate 15. The length of the portion of the non-clastic adhesive tapes 20 and 30 that is bonded to the elastic laminate 15 is generally about 5 mm and the total length of the non-elastic adhesive tape is generally about 20 mm to 40 mm, preferably 25 to 30 mm. The length of the elastic laminate in its relaxed state is typically 20 to 40 mm, preferably 25 to 35 mm. The non-elastic adhesive tapes 20 and 30 each comprise a fibrous layer 21 of nonwoven thermoplastic polymer fibers and an adhesive layer 22 by which the non-elastic adhesive tapes are bonded to the elastic laminate 15. Further, non-elastic adhesive tape 30 in FIG. 1 has a finger lift 31 attached to it at the end opposite to the end that is attached to the elastic laminate 15. Finger lift 31 is typically a film of about 3 to 5 mm that covers the adhesive of the non-elastic adhesive tape 30 at one end. When mounted to an absorbent article such as a diaper, the adhesive closure tape tab 10 can be adhered to edge portion 140 of the diaper 1 with non-elastic adhesive tape 20. Non-elastic adhesive tape 30 can then be used to close the diaper by adhering non-elastic adhesive tape 30 to the target zone 150 at the front of the diaper (see FIG. 1).

Figure 3:
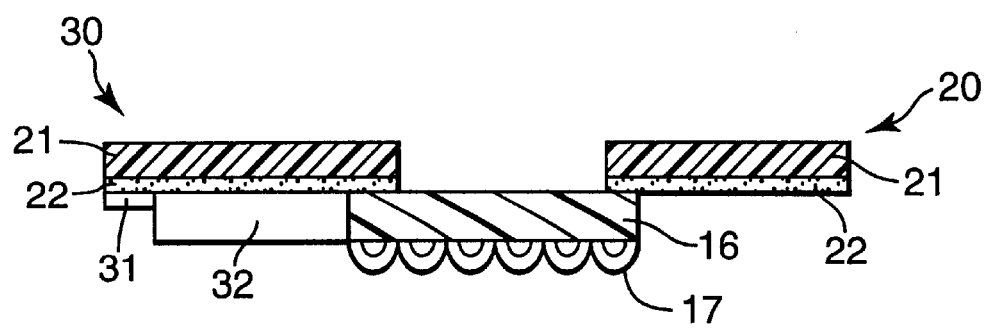

According to a variant of the embodiment shown in FIG. 2, the adhesive closure tape tab may include a component of a hook and loop fastening system. Such an embodiment is shown in FIG. 3. As can be seen in FIG. 3, the non-elastic adhesive tape 20 has a hook component 32 of a hook and loop fastening system. This hook component 32 is bonded to the adhesive layer 22 of non-elastic adhesive tape 30 and covers the adhesive layer between the of elastic laminate 15 and the finger lift 31. If finger lift 31 is not used, the hook component will extend to the end of non-elastic adhesive tape 30.

Figure 4:
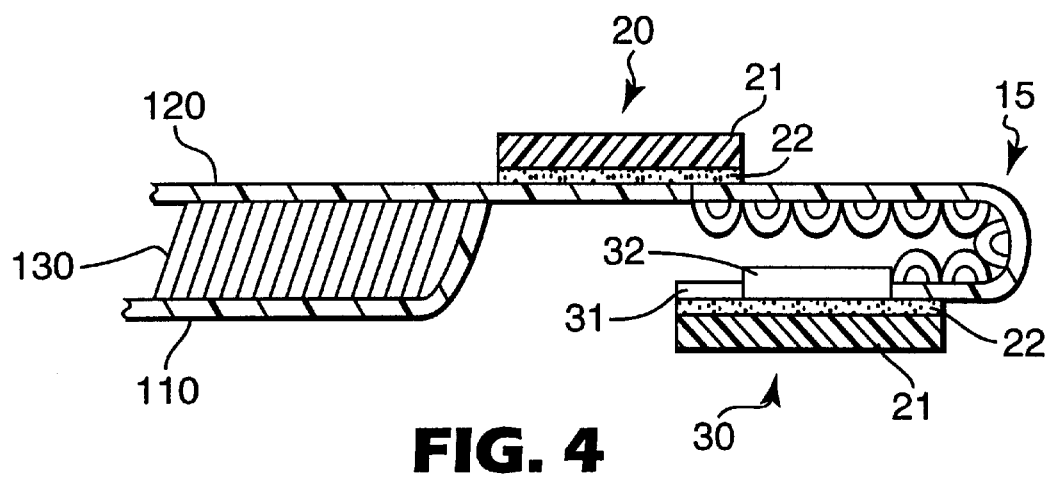
FIGS. 4 and 5 schematically illustrate two configurations of an adhesive closure tape tab of FIG. 3 attached to an edge portion of a disposable absorbent article during storage prior to usage.
Figure 5:
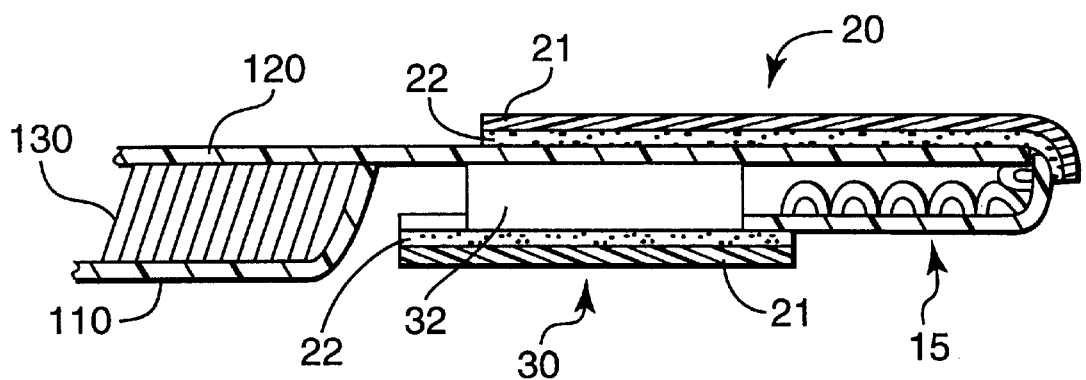

The adhesive closure tape tab of FIG. 3 can be secured to an absorbent article and folded prior to usage of the absorbent article as shown in FIGS. 4 and 5. As shown in FIG. 4, the non-elastic adhesive tape 20 of the adhesive closure tape tab of FIG. 3 is bonded to edge portion 140 of diaper 1. In the embodiment shown in FIG. 4, the adhesive closure tape tab is folded such that the hook component 32 faces the expandable fibrous layer 17 of the elastic laminate 15 and may releasably engage therewith. The folded adhesive closure tape tab in FIG. 4 extends beyond edge portion 140 of diaper 1. In an alternative embodiment shown in FIG. 5, the adhesive closure tape tab is folded around edge portion 140 of diaper 1 which is generally more convenient for packaging and handling of diapers 1. As seen in FIG. 5, the hook component 32 now faces the side of edge portion 140 that is opposite to the side of edge portion 140 to which non-elastic adhesive tape 20 of the adhesive closure tape tab is adhered.

Figure 6:
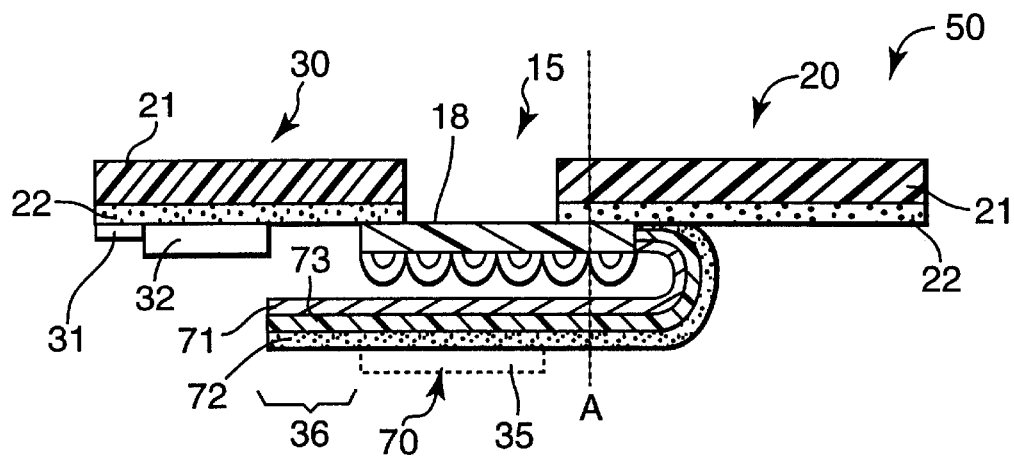
FIGS. 6, 8 and 9 illustrate further embodiments of an adhesive closure tape tab according to the invention.

FIG. 6 shows a further embodiment of an adhesive closure tape tab according to the invention. The adhesive closure tape tab 50 shown in this figure further includes a release tape 70 comprising on one side of a backing 73, for example a film backing, a release layer 71, or alternatively a release surface, and on the opposite side an adhesive layer 72. The release tape 70 is bonded to the non-elastic adhesive tape adjacent the edge of elastic laminate 15. Release tape 70 is folded such that release layer 71 overlays the elastic laminate 15. Release tape 70 covers the elastic laminate 15 and adhesive area 36 between hook component 32 and the elastic laminate 15. As a release tape, any release tape having a support sheet with an adhesive layer on one major side and a release surface at the opposite major side can be used.

Figure 7:
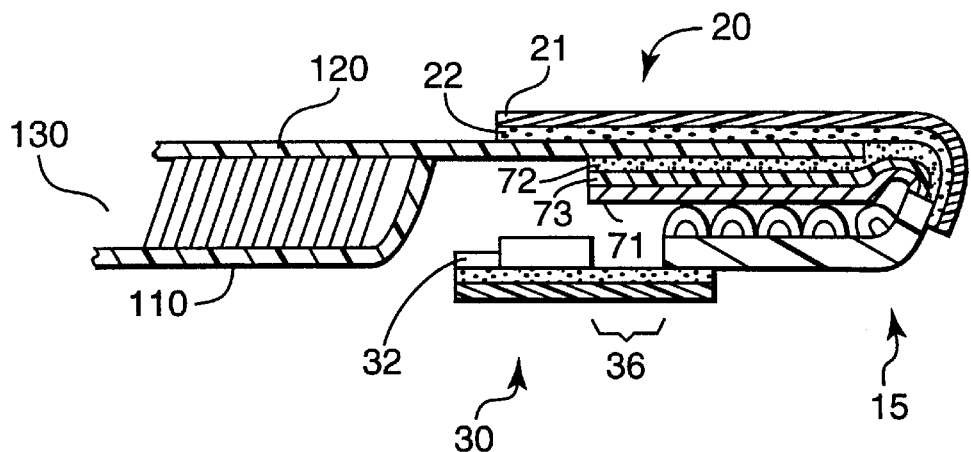
FIG. 7 illustrates the adhesive closure tape tab of FIG. 6 attached to an edge portion of a disposable absorbent article during storage prior to usage.

FIG. 7 illustrates the use of adhesive closure tape tab 50 on a diaper. Adhesive closure tape tab 50 is bonded with non-elastic adhesive tape 20 to outside surface 120 of edge portion 140 of the diaper. Adhesive closure tape tab 50 is folded along line A (FIG. 6) and release tape 70 adheres to inside surface 110 of edge portion 140. Accordingly, during storage, release tape 70 protects adhesive portion 36 from contamination. When opening the folded closure tape tab 50 for use, the release tape 70 will remain on the inside surface 110 and the adhesive portion 36 will adhere to target zone 150 and support the mechanical fastening system. After use, the diaper can be folded or rolled into a structure, such that the adhesive closure tape tab still extends outwardly from the rolled up diaper. The adhesive section 36 is then secured to the target area 150 or to the outside surface 120 or the diaper so as to secure the diaper in its rolled up configuration in which form it may be easily and conveniently disposed in a waste receptacle. The adhesive closure tape tab 50 of the present invention however does not need to be provided with the adhesive section 36 to secure, the diaper prior to disposal. In case the adhesive section 36 is not present, the hook portion or the adhesive closure tape tab on one edge portion of the diaper may be engaged with the fibrous layer of the adhesive closure tape tab at the opposite edge portion of the diaper, or the fibrous backsheet or any other fibrous surface, to secure the diaper in a folded configuration prior to disposal.

Further, it will be understood by one skilled in the art that as a further variant, the closure system of the adhesive closure tape tab 50 may not use a component of a hook and loop fastening system but may instead rely on the adhesive of non-elastic adhesive tape 30 for closure. In such an embodiment, the release tape 70 would extend sufficiently to cover the adhesive layer of non-elastic adhesive tape 30 during storage.

As further shown in FIG. 6, the adhesive closure tape tab 50 may also optionally comprise a liner 35 that covers the adhesive layer of release tape 70 at least to the extend that the adhesive layer of the release tape 70 would contact the elastic laminate at its major side 18 between the non-elastic adhesive tapes 20 and 30 when two or more adhesive closure tape tabs 50 are overlaying each other such as in a stack or when the adhesive closure tape tab 50 is to be cut from a roll of prelaminated composite tape as described furtheron. Prior to using such an adhesive closure tape tab 50 in the diaper manufacturing, the release liner 35 may be removed.

Figure 8:
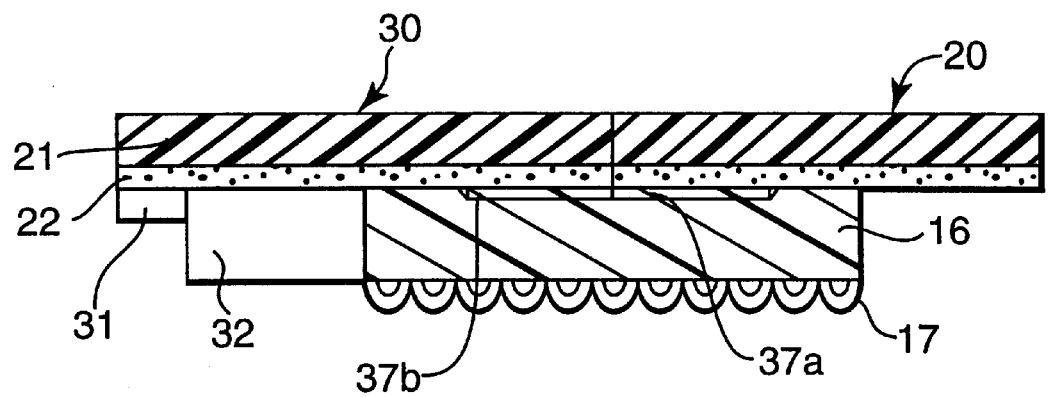

FIG. 8 illustrates a further embodiment of an adhesive closure tape tab according to the invention. In this embodiment, the non-elastic adhesive tapes 20 and 30 are adhered to the elastic laminate 15 so as to contact each other. Also, covering layers 37a and 37b, e.g. film layers, are provided that cover the adhesive of the non-elastic adhesive tape over a portion at the edges of the tapes that are contacting each other. Accordingly, the non-elastic adhesive tapes 20 and 30 would only be bonded to the opposite ends of the elastic laminate and they would not be bonded to the elastic laminate where the non-elastic adhesive tapes are contacting each other. When the closure tape tab is stretched, the non-elastic adhesive tapes 20 and 30 would move away from each other leaving a gap in between them. When the elastic laminate is again allowed to relax, the non-elastic adhesive tapes 20 and 30 would substantially contact each other again. The covering layers 37a and 37b allow the elastic laminate to be stretched without being hindered by the non-elastic adhesive tapes adhered thereto. As an alternative to the use of covering layers 37a and 37b, the adhesive layer of the non-elastic adhesive tapes may be provided such as to not extend over the full length of the tape thereby leaving a portion on the tape that does not contain adhesive. This embodiment provides the advantage that when such adhesive closure tape tabs are overlying each other in a stack or roll, the use of a release liner 35 in FIG. 6 can be avoided because the fibrous layer of the non-elastic adhesive tapes could be coated with a release coating thereby preventing permanent adherence of the adhesive layer of the release tape to the fibrous layer of the non-elastic adhesive tape.

Figure 9:
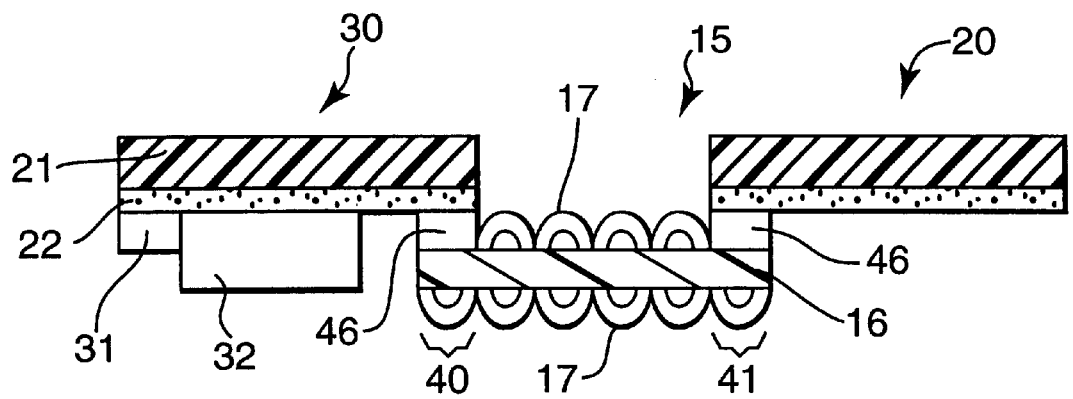

FIG. 9 further illustrates an adhesive closure tape tab in which the elastic laminate has expandable fibrous layers 17 on both sides of the elastic film 16. In this embodiment, a zone 40 and 41 would be left at both ends of one side of the elastic film so as to adapt the elastic film for bonding the non-elastic adhesive tapes 20 and 30 thereto. These zones 40 and 41 can be created by zone melting the fibrous layer 17 at these spots. Also, a tie layer 46 may be provided in these zones to improve the bonding of the non-elastic adhesive tapes 20 and 30 to the elastic laminate. Such a tie layer may for example comprise an ethylene vinyl acetate (co)polymer.

Figure 10:
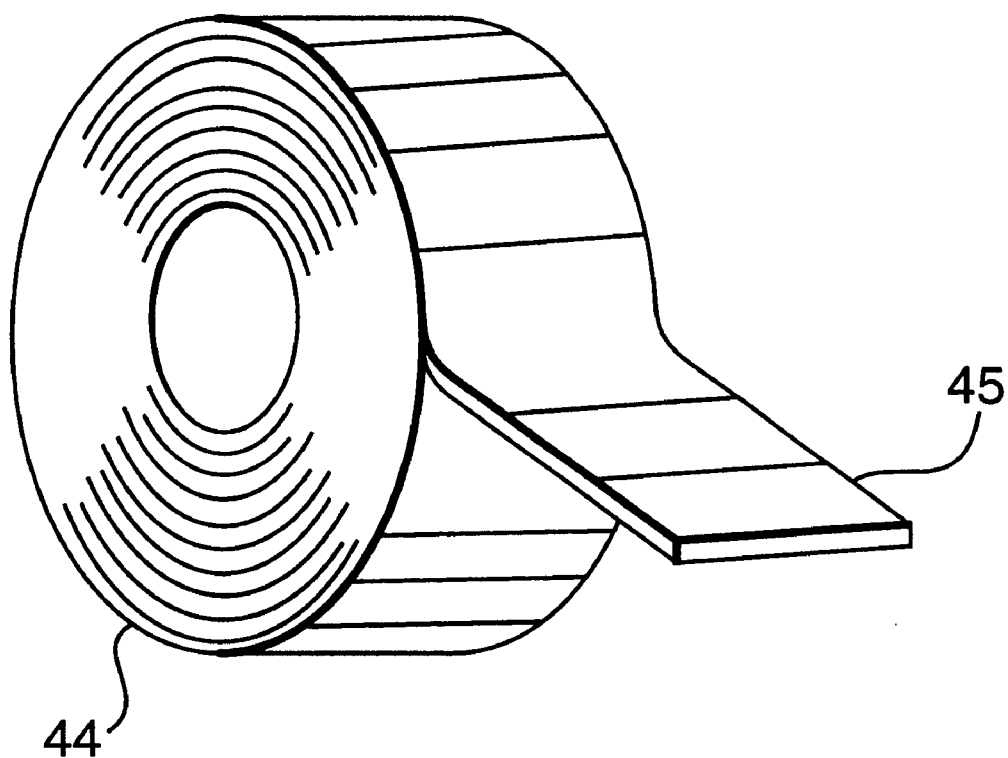
FIG. 10 illustrates a prelaminated composite tape in roll form.

According to a preferred embodiment of the present invention, the adhesive closure tape tab as described in any of the embodiments above, can be cut from a stock roll of a prelaminated composite tape. Thus, as shown in FIG. 10, a prelaminated composite tape in stable roll form 44 is provided. A segment 45 as desired can be cut from the roll. The length of the segment 45 will determine the width of the adhesive closure tape tab cut from the roll and the width of the roll will determine the length of the adhesive closure tape tab. Thus, the non-elastic adhesive tapes and elastic laminate of the adhesive closure tape tab will extend axially in the roll of the prelaminated composite tape.

What is claimed is:

1. An adhesive closure tape tab (10,50) comprising an elastic laminate (15) comprising an elastic film (16) having on at least a first major side an expandable fibrous layer (17) of non-woven thermoplastic polymer fibers and on a second major side, a first (30) and a second (20) non-elastic adhesive tape, each adhesive tape comprising a fibrous layer (21) of non-woven thermoplastic polymer fibers having on one major surface an adhesive layer (22), said first (30) and second (20) non-elastic adhesive tapes being attached opposite to each other and said second major side of said elastic laminate (15) by said adhesive layer (22) and said first (30) and second (20) non-elastic adhesive tape extending beyond said elastic laminate (15).

2. An adhesive closure tape tab according to claim 1 wherein said first non-elastic adhesive tape comprises a mechanical fastener (32) adhered to said adhesive layer (22).

3. An adhesive closure tape tab according to claim 1 further comprising a release tape (70) having a backing (73) having an adhesive layer (71) on one side and a release surface (72) on the side opposite thereto, said release tape being bonded to said second non-elastic adhesive tape (70) adjacent said elastic laminate and being folded such that said release surface overlays the expandable fibrous layer (17) of said elastic laminate (15).

4. An adhesive closure tape tab according to claim 1 wherein said first and second non elastic adhesive tape (20,30) each comprise a covering layer (37a, 37b) covering the adhesive layer of the non elastic adhesive tape adjacent the edge overlaying the elastic laminate (15) and wherein said first and second non-elastic adhesive tape (20,30) are bonded to said elastic laminate (15) in such a way that in the non-expanded state of said adhesive closure tape tab, the first and second non-elastic adhesive tape (20,30) are in contact with each other.

5. An adhesive closure tape tab according to claim 1 wherein said second major side of said elastic laminate (15) also includes an expandable fibrous layer (17) of non-woven thermoplastic polymer fibers attached thereto and wherein said second major side of said elastic laminate is adapted at opposite ends (40,41) to improve the bonding of said first and second non-elastic adhesive tape thereto.

6. A prelaminated composite tape laminate in stable roll (44) from which an adhesive closure tape tab can be cut the laminate comprising an elastic laminate (15) comprising an elastic film (16) having on at least a first major side an expandable fibrous layer (17) of non-woven thermoplastic polymer fibers and on the second major side, a first (30) and a second (20) non-elastic adhesive tape, each adhesive tape comprising a fibrous layer (21) of non-woven thermoplastic polymer fibers having on one major surface an adhesive layer (22), said first (30) and second (20) non-elastic adhesive tape being attached opposite to each other on said second major side of said elastic laminate (15) by said adhesive layer (22) and said first (30) and second (20) non-elastic adhesive tape extending beyond said elastic laminate (15) and in which said first and second non-elastic adhesive tape and said elastic film extend axially.

7. An absorbent article (1) having an adhesive closure tape tab (10,50) according to claim 1 attached to one edge.

* * * * *

UNITED STATES PATENT AND TRADEMARK OFFICE
CERTIFICATE OF CORRECTION

PATENT NO. : 6,719,744 B2
DATED : April 13, 2004
INVENTOR(S) : Kinnear, Christopher M.

It is certified that error appears in the above-identified patent and that said Letters Patent is hereby corrected as shown below:

Column 1,
Line 62, after "vantage that" and before "skin of the wearer", please delete "tie" and insert -- the --.

Column 3,
Line 58, after the word "require", please insert -- use --.

Column 4,
Line 11, after the word "minimize", please insert -- the --.

Column 5,
Line 28, after the words "prepared as" and before "above", please delete "describe" and insert -- described --.
Line 56, after the phrase "the adhesive layer of", please insert -- one of --.

Column 7,
Line 1, after the phrase "diaper is", please delete "complaint" and insert -- complaint --.
Line 56, please delete "non-clastic" and insert -- non-elastic --.

Column 8,
Line 17, after the phrase "adhesive layer between the", please insert -- edge --.
Line 19, after the phrase "component with", please insert -- generally --.
Line 66, after the phrase "the outside surface 120", plese delete "or" and insert -- of --.

Column 9,
Line 6, after "portion", please delete "or" and insert -- of --.

UNITED STATES PATENT AND TRADEMARK OFFICE
CERTIFICATE OF CORRECTION

PATENT NO. : 6,719,744 B2
DATED : April 13, 2004
INVENTOR(S) : Kinnear, Christopher M.

It is certified that error appears in the above-identified patent and that said Letters Patent is hereby corrected as shown below:

<u>Column 10,</u>
Line 26, after the phrase "major surface", please delete "an" and insert -- and --.

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

PATENT NO.    : 6,719,744 B2
DATED         : April 13, 2004
INVENTOR(S)   : Kinnear, Christopher M.

It is certified that error appears in the above-identified patent and that said Letters Patent is hereby corrected as shown below:

Column 1,
Line 62, after "vantage that" and before "skin of the wearer", please delete "tie" and insert -- the --.

Column 3,
Line 58, after the word "require", please insert -- use --.

Column 4,
Line 11, after the word "minimize", please insert -- the --.

Column 5,
Line 28, after the words "prepared as" and before "above", please delete "describe" and insert -- described --.
Line 56, after the phrase "the adhesive layer of", please insert -- one of --.

Column 7,
Line 1, after the phrase "diaper is", please delete "complaint" and insert -- compliant --.
Line 56, please delete "non-clastic" and insert -- non-elastic --.

Column 8,
Line 17, after the phrase "adhesive layer between the", please insert -- edge --.
Line 19, after the phrase "component will", please insert -- generally --.
Line 66, after the phrase "the outside surface 120", plese delete "or" and insert -- of --.

Column 9,
Line 6, after "portion", please delete "or" and insert -- of --.

UNITED STATES PATENT AND TRADEMARK OFFICE
CERTIFICATE OF CORRECTION

PATENT NO. : 6,719,744 B2
DATED : April 13, 2004
INVENTOR(S) : Kinnear, Christopher M.

It is certified that error appears in the above-identified patent and that said Letters Patent is hereby corrected as shown below:

Column 10,
Line 26, after the phrase "major surface", please delete "an" and insert -- and --.

This certificate supersedes Certificate of Correction issued December 21, 2004.

Signed and Sealed this

Twenty-ninth Day of March, 2005

JON W. DUDAS
*Director of the United States Patent and Trademark Office*